United States Patent [19]
Polanco

[11] Patent Number: 5,087,196
[45] Date of Patent: Feb. 11, 1992

[54] DUAL COIL SPRING LINGUAL ARCH

[76] Inventor: Julio R. Polanco, 3242 Kimber Ct. #42, San Jose, Calif. 95124

[21] Appl. No.: 740,719

[22] Filed: Aug. 6, 1991

[51] Int. Cl.⁵ .................................................. A61C 3/00
[52] U.S. Cl. ..................................... 433/21; 433/18; 433/7
[58] Field of Search .................... 433/7, 18, 20, 21, 22

[56] References Cited

U.S. PATENT DOCUMENTS

| | | | |
|---|---|---|---|
| 2,318,001 | 5/1943 | Linde | 433/21 |
| 4,468,196 | 8/1984 | Keller | 433/7 |
| 4,571,178 | 2/1986 | Rosenberg | 433/18 |

Primary Examiner—Cary E. O'Connor
Attorney, Agent, or Firm—Michael J. Hughes

[57] ABSTRACT

A dual coil lingual arch (10) appliance for use in the field of orthodontics is disclosed. Molar teeth (36, 38) are displaced distally by means of a primary wire arch (14) while anterior teeth (40) are displaced forward by means of a secondary wire arch (20). The primary wire arch (14) may be attached to the molar teeth (36, 38) by means of a pair of molar bands (42, 44), and the secondary wire arch (20) is attached to the primary wire arch (14) at a pair of spring junctions (30, 32). Near the spring junctions (30, 32) the secondary wire arch (20) is wound around the primary wire arch (14) to form a pair of spring coils (24, 26). In use, after the primary wire arch (14) is anchored to the molar teeth (36, 38) the secondary wire arch is activated by a practitioner by the action of lengthening the spring coils (24, 26), whereas the pressure on the molar teeth (36, 38) is independently set by means of preforming the primary wire arch (14). Thus, the amount of force applied to the anterior teeth (40) is independent of the amount of force applied to the molar teeth (36, 38).

20 Claims, 2 Drawing Sheets

DUAL COIL SPRING LINGUAL ARCH

TECHNICAL FIELD

The present invention relates generally to the field of dentistry and more particularly to an improved lingual arch for use in the specialty of orthodontics. The predominant current usage of the dual coil spring lingual arch of the present invention is as an orthodontic appliance.

BACKGROUND ART

The field of orthodontics has changed significantly over the past several decades. A substantial part of this change is due to the development of improved appliances for use in the field. Old fashioned "braces" have been largely replaced by improved appliances such as that described in U.S. Pat. No. 4,354,833, issued to Fijita and that described in U.S. Pat. No. 4,571,179, issued to Balenseifen. Such modern appliances are usually placed on the interior ("lingual") side of the teeth and thus are not visible when installed. This feature alone greatly increases the willingness of patients to have the devices put into place, and thus increases the incidence of successful treatment.

A variety of different appliances is required in order to properly treat the various problems of different dental patients. For example, a common type of problem is a malocclusion wherein the front ("anterior") top ("maxillar") teeth protrude to excess. A more basic problem is that of "overcrowding" wherein there is not sufficient room for later developing teeth to inhabit the mouth. This problem can occur in the maxillar or the lower ("mandibular") teeth. Such overcrowding may result in the above described type of malocclusion or, depending upon the individual, in any number of other unhealthy misalignments of the teeth. Given the great variety of peculiarities which are encountered, many appliances have been developed for creating specific types of adjustments of the teeth. An example of such a specific device is found in U.S. Pat. No. 4,592,725, issued to Goshgarian, which teaches a bar for connecting between molars and for performing various realignment procedures thereon. U.S. Pat. No. 4,854,864, issued to Cleary teaches an orthodontic bracket and bar combination system which, also, is an improvement well suited to its specified purposes.

A development related to the above described improvements has been the need for improved methods for attaching appliances, such as those described herein, to the teeth. An example of such an improvement is found in U.S. Pat. No. 4,799,883, issued to Stoller et al.

A not uncommon requirement is for a device to move the anterior teeth forward and at the same time move the molars distally, thus creating spaces for new permanent teeth to erupt. Various types of appliances and combinations thereof, including some of those mentioned previously herein, have been applied to this purpose. However, some orthodontists have been frustrated by the lack of an appliance which can quickly and easily be positioned to perform this combined function which appliance is readily adaptable to a variety of mouth sizes and peculiarities. Furthermore, given the differences between individuals, it is desirable to be able to separately adjust the pressure applied to the anterior teeth distinct from the adjustment of pressure applied to the molars. An additional factor is that some prior art orthodontic appliances, while they might in fact be adaptable to the above specified purposes, are more cumbersome, expensive, and difficult to install and adjust than is required to accomplish just those purposes.

All of the prior art orthodontic appliances or combinations thereof which are capable of moving anterior teeth forward while moving molars distally, within the inventor's knowledge, have been adapted to fit specific sizes and or configurations of mouths and teeth, or else have been incapable of being adjusted to independently regulate pressure applied to the anterior teeth, or else have required more than a single appliance to accomplish this combined purpose.

No prior art orthodontic appliance, to the inventor's knowledge, has been easily adaptable to successfully provide the above described combination of desirable qualities. In any event, the inventor is aware of instances in which no appliance known to the inventor has been found to be well suited to those instances. All prior art orthodontic appliances have been found wanting in at least one of these qualities in at least some applications.

DISCLOSURE OF INVENTION

Accordingly, it is an object of the present invention to provide an orthodontic appliance for moving the anterior teeth forward while moving the molars distally.

It is another object of the present invention to provide an orthodontic appliance wherein pressure applied to anterior teeth can be adjusted independently in relation to pressure applied to the molars.

It is still another object of the present invention to provide an orthodontic appliance which is easily adapted to a great variety of mouth sizes and tooth configurations.

It is yet another object of the present invention to provide an orthodontic appliance which is easy to install initially and, further, which is easy to readjust as required after being installed.

It is still another object of the present invention to provide an orthodontic appliance which is inexpensive to manufacture.

It is yet another object of the present invention to provide an orthodontic appliance for moving anterior teeth forward and moving molars distally which is no larger or more complicated than is required by the prescribed combined purpose.

It is still another object of the present invention to provide an orthodontic appliance which is comfortable to the patient and is not unsightly.

It is yet another object of the present invention to provide an orthodontic appliance which delivers a gentle pressure against the teeth that is constant but not massive.

Briefly, the preferred embodiment of the present invention is a dual coil spring lingual arch having a primary spring loop for attachment at its ends to opposed molar teeth such that those molar teeth tend to be pushed apart distally. A secondary spring loop has, near each of its ends, a coil, which coil is wrapped around the primary spring loop. Each of the ends of the secondary spring loop is rigidly affixed to the primary spring loop. In an inactivated position the secondary spring loop is generally congruent with or behind the closed end of the primary spring loop. After the primary spring loop is in place in the mouth and affixed to the molars, the secondary spring loop is activated by extending the coils past the limits of their elasticity such that they do not completely return to their original shape. Thus extending the coils causes the closed end of the secondary spring loop to push against the anterior teeth, the amount of which pressure is adjustable according to how far the coils are extended.

An advantage of the present invention is that the anterior teeth can be moved forward while the molars are moved distally, using a single appliance.

A further advantage of the present invention is that pressure applied to anterior teeth can be adjusted independently in relation to pressure applied to the molars.

Yet another advantage of the present invention is that it is not preformed to an expected configuration, and thus is easily adapted to a great variety of mouth sizes and shapes.

Still another advantage of the present invention is that it is easy to install and easy to adjust, as required, after installation.

Yet another advantage of the present invention is that it is inexpensive to manufacture.

Still another advantage of the present invention is that it is comfortable and unobtrusive in use.

These and other objects and advantages of the present invention will become clear to those skilled in the art in view of the description of the best presently known modes of carrying out the invention and the industrial applicability of the preferred embodiments as described herein and as illustrated in the several figures of the drawing.

BEST MODE FOR CARRYING OUT INVENTION

The best presently known mode for carrying out the invention is a dual coil lingual arch. The predominant expected usage of the inventive dual coil lingual arch is in the field of orthodontics, particularly in children and young adults wherein the ability to spread existing teeth so as to make room for the emergence of new teeth is most desirable.

Figure 1:
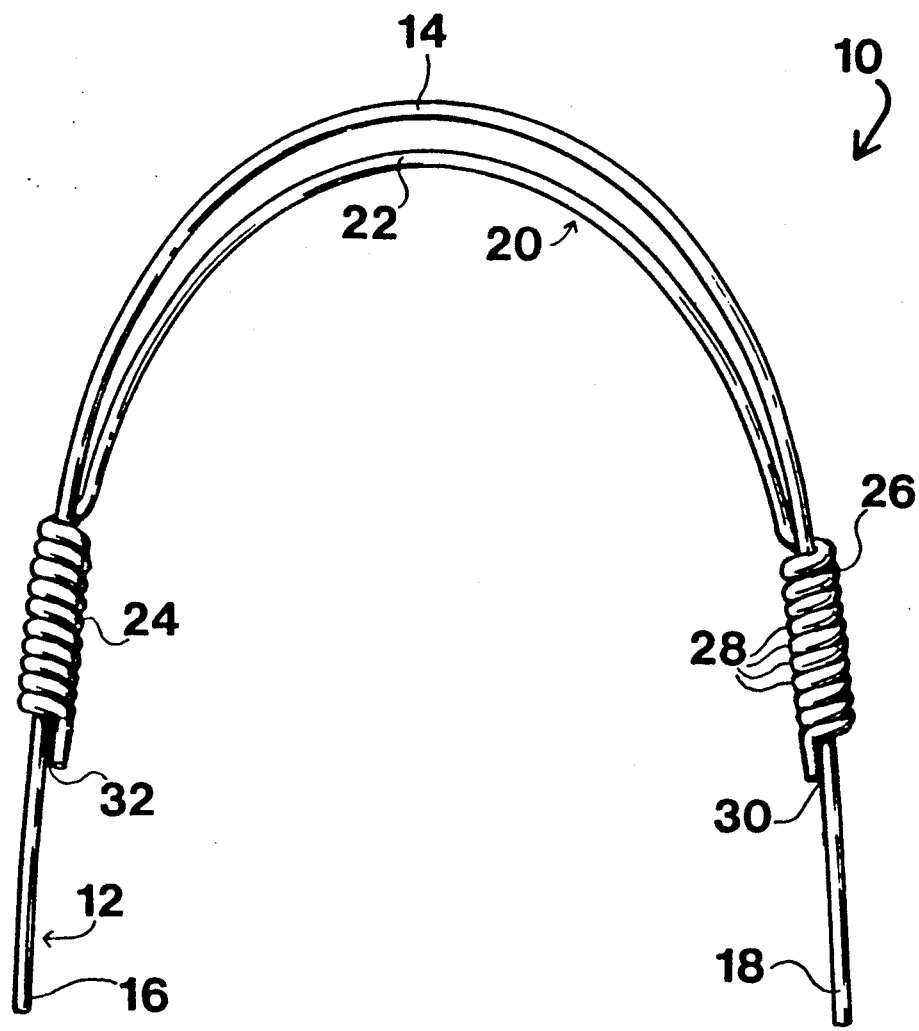
FIG. 1 is a top plan view of a dual coil spring lingual arch, according to the present invention.

The dual coil lingual arch of the presently preferred embodiment of the present invention is illustrated in a top plan view in FIG. 1 and is designated therein by the general reference character 10. In many of its substantial components, the dual coil lingual arch 10 does not differ significantly from conventional orthodontic appliances. The physical structure is similar is some respects to that of prior art appliances such as that illustrated and described in U.S. Pat. No. 4,854,864, issued to Cleary. The dual coil spring lingual arch lo has a primary wire arch 12 which is not unlike the conventional lingual arch portion of the Cleary invention. As can be seen in the drawing of FIG. 1, the primary wire arch 12 is formed roughly in the shape of a horseshoe (or a "U") with a curved primary wire arch anterior portion 14, a left end portion 16 and a right end portion 18. In the best presently known embodiment 10 of the invention the primary wire arch 12 is constructed from 0.091 cm (0.036 inch) stainless steel spring wire.

The best presently known embodiment 10 of the present invention also has a secondary wire arch 20. The secondary wire arch 20 has a secondary wire arch anterior portion 22, which approximates the curve of the primary wire arch anterior portion 14, a left spring coil 24 and a right spring coil 26. The coil springs 24 and 26 are formed by wrapping the ends of the secondary wire arch 20 around the primary wire arch 12, as is shown in the drawing. In the best presently known embodiment 10 of the invention, each of the coil springs 24 is formed with ten each of wraps ("loops") 28 around the primary wire arch 14, although the inventor has found that the invention functions well with more or fewer of the loops 28. The secondary wire arch 20 is joined to the primary wire arch 12 at a left spring junction 30 and a right spring junction 32, in the presently preferred embodiment 10 of the invention, by means of soldering, although alternative joining means such as welding might be used. In the best presently known embodiment 10 of the invention, the secondary wire arch 20 is formed of 0.051 cm (0.020 inch) stainless steel spring wire.

Figure 2:
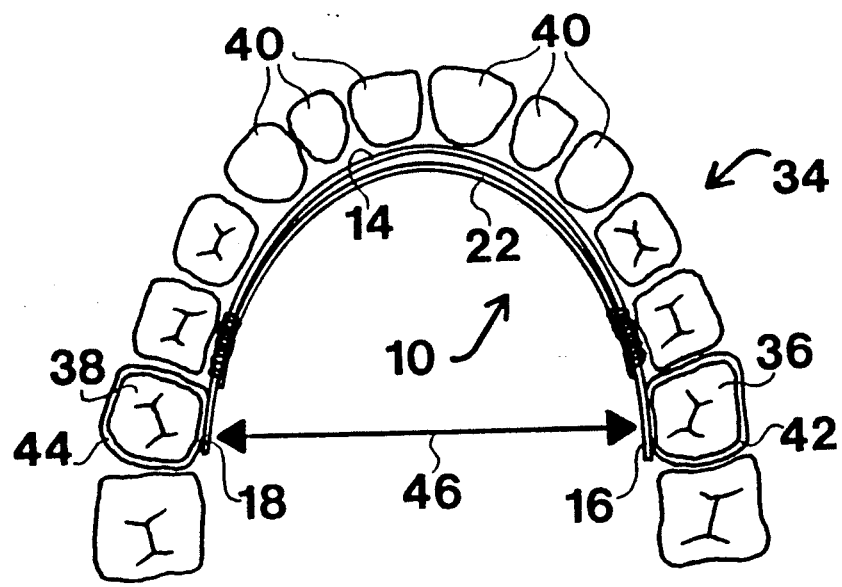
FIG. 2 is a bottom plan view of the dual coil spring lingual arch of FIG. 1, installed on upper teeth in a mouth and in a pre-activation mode.

Referring now to FIG. 2, the inventive dual coil spring lingual arch 10 is depicted in a bottom plan view positioned within a dental set 34. The dental set 34 in the example of FIG. 2 is an upper dental set although, as described herein, the dual coil spring lingual arch 10 may be applied to the upper dental set 34, as illustrated, or to a lower dental set (not shown). Further designated in the view of FIG. 2 are a left anchor molar 36, a right anchor molar 38 and plurality (six, in the example of FIG. 2) of anterior teeth 40. It should be noted that the view of FIG. 2 is exemplary in nature, and that the term "anchor molar" in relation to the left anchor molar 36 and the right anchor molar 38 is used herein to designate those teeth to which the dual coil spring lingual arch 10 is to be "anchored", as will be described in more detail hereinafter. A more specific term is specifically not used to designate the anchor molars 36 and 38 because, at the discretion or the practitioner and according to the needs of the patient, the anchor molars 36 and 38 may be chosen to be any distally opposed pair of molar teeth, including but not limited to those exemplified in FIG. 2.

The primary wire arch left end 16 is affixed to a left molar band 42, and the primary wire arch right end 18 is affixed to a right molar band 44. The molar bands 42 and 44 are not unique to the present invention. Indeed, any molar band type, including those currently in use and those which might be developed in the future, might be used in conjunction with the inventive dual coil spring lingual arch 10. Furthermore, the inventive dual coil spring lingual arch 10 may be rigidly affixed to the molar bands 42 and 44 by means of soldering or the like or, alternatively, the dual coil spring lingual arch may be removably attached to the molar bands 42 and 44 by means such as, for example, those taught by the aforementioned Stoller patent. In the illustration of the best presently known embodiment 10 of the invention of FIG. 2, the dual coil spring lingual arch 10 is shown rigidly affixed to the molar bands 42 and 44 by means of soldering. The molar bands 42 and 44 are affixed in conventional fashion to the left anchor molar 36 and the right anchor molar 38, respectively. It should be noted that alternative conventional means for anchoring the inventive dual coil spring lingual arch 10 to the anchor molars 36 and 38 which do not include the molar bands 42 and 44 might be employed in conjunction with the present invention, should the practitioner deem such alternative means adequate for a particular application.

In accord with its purpose, the primary wire arch 14 is compressed so as to provide a force tending to push apart the molars 36 and 38 as indicated by the dual headed arrow 46. The amount of such force is finally determined by a practitioner, prior to putting the dual coil spring lingual arch 10 in place, by adjustment of the unstressed shape of the primary wire arch 14. It should be noted that, as can be seen in the view of FIG. 2, the primary wire arch 14 may also press against molar teeth not specifically enumerated herein, depending upon the shape of the patient's mouth and the adjusted shape of the primary wire arch 14.

Figure 3:
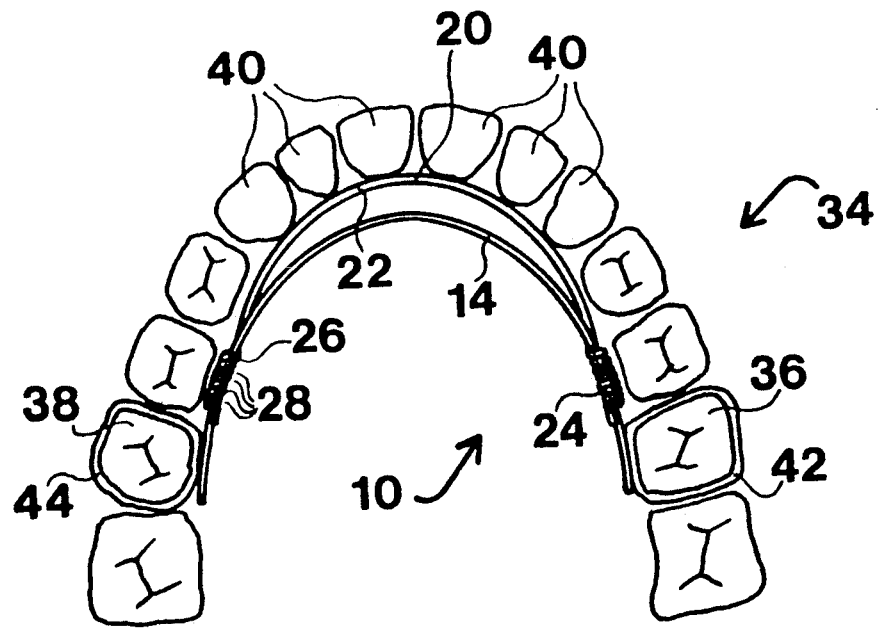
FIG. 3 is a bottom plan view, similar to the view of FIG. 2, showing the dual coil spring lingual arch in a post-activation mode.

In the view of FIG. 2, the secondary wire arch 20 is shown in an inactivated mode. In contrast, the view of FIG. 3 shows the dual coil spring lingual arch 10 with the secondary wire arch 20 in an activated mode. In order to achieve this activated mode, the practitioner extends the spring coils 26 and 28 past their point of perfect elasticity such that the unstressed lengths of the spring coils 26 and 28 are increased, thus moving the secondary wire arch anterior portion 22 against the anterior teeth 40. As has been described heretofore, in the best presently known embodiment 10 of the present invention, the dual coil spring lingual arch is "anchored" to the anchor molars 36 and 38 by means of the molar bands 43 and 44 thus effectively preventing movement of the primary wire arch 12 either forward or backward in relation to the dental set 34. Therefore, the secondary wire arch anterior portion 22 pushes forward against the anterior teeth 40 relative to the anchor molars 36 and 38 with a force proportional to the spring rate of the material from which the secondary wire arch 20 is constructed, with the absolute value of such force being finally determined by the unstressed length of the spring coils 24 and 26 as adjusted by the practitioner.

As is shown above, in great part, the dual coil spring lingual arch 10 according to the present invention resembles prior art conventional orthodontic appliances in some respects. Among the substantial differences are the inclusion of the secondary wire arch 20 and related features which allow forward pressure against the anterior teeth 40 and distal pressure against the anchor molars 36 and 38 to be applied by a single appliance and further to be separately and independently adjusted. No significant changes of materials are envisioned nor are any special constructions required.

Various modifications may be made to the invention without altering its value or scope. For example, the material content from which the primary wire arch 12 and the secondary wire arch 20 are constructed might be varied, as might the diameters of the material wire. Similarly, while the parts of the invention are described herein as being joined by soldering, other joining means might be used. Likewise, the number of loops 28 in each of the sprint coils 24 and 26 might be varied from the example of the best presently known embodiment 10 of the present invention.

Another conceivable change would be to combined the inventive dual coil spring lingual arch 10 with other appliances or parts thereof such that the inventive characteristics are retained. Yet another conceivable change would be to make incidental changes to alter the appearance of the inventive dual coil spring lingual arch 10 or to add ancillary features.

All of the above are only some of the examples of available embodiments of the present invention. Those skilled in the art will readily observe that numerous other modifications and alterations may be made without departing from the spirit and scope of the invention. Accordingly, the above disclosure is not intended as limiting and the appended claims are to be interpreted as encompassing the entire scope of the invention.

INDUSTRIAL APPLICABILITY

The dual coil spring lingual arch 10 of the present invention is intended to be widely used as an orthodontic appliance. The predominant current usages are for the rearranging of the teeth of young persons, as required, to provide room for the emergence of new teeth. The dual coil lingual arch 10 of the present invention is intended primarily for placement in the palate for adjustment of the dental set 34.

Because the tension separating the ends of the primary spring loop 14 is controlled by the elastic properties of the primary spring loop 14 and by the unstressed shape thereof, while the forward tension against the anterior teeth 40 is independently controlled by the elastic properties of the secondary spring loop 20 and the unstressed shape thereof, the dual coil spring lingual arch 10 is adaptable to a great variety of applications. Furthermore, since the shape of the dual coil spring lingual arch 10 is not generalized to conform to any anticipated mouth configuration, as are some prior art devices, it is expected that practitioners will be able to adapt the inventive dual coil spring lingual arch 10 for use even in those patients requiring non-standard appliance configurations.

The inventive dual coil spring lingual arch 10 may be used alone, or in combination with other orthodontic appliances, as required. Installation of the dual coil spring lingual arch lo requires no special training, and any orthodontist or dentist who is familiar with orthodontic practices should be able to practice the invention, given the disclosure herein. Installation of the dual coil spring lingual arch 10 is accomplished by securing the primary wire arch left end 16 and the primary wire arch right end 18 to the anchor molars 36 and 38, respectively, using conventional methods such as the molar bands 42 and 44. The primary wire arch left end 16 and the primary wire arch right end 18 may be trimmed to length, as required by the application. Then the secondary wire arch 20 is activated as has been heretofore described using conventional wire pliers such as, for example, dulled pin cutters and conventional "HOW" pliers (a common dental tool). Because the secondary wire arch 20 is somewhat flexible, it will conform easily to the anterior teeth 40, even when such anterior teeth 40 are not well aligned.

It should be noted that in those instances which require that the anterior teeth 40 be adjusted but no adjustment of the anchor molars 36 and 38 is required, the primary wire arch 14 may be formed, prior to installation, such that its unstressed shape is not unlike the shape that it will be required to attain when in place in the patient's mouth. Similarly, since the force placed on the anterior teeth 40 by the secondary wire arch 20 may be readjusted after the dual coil spring lingual arch 10 is in place, it may also be readjusted during the course of the treatment. Such force on the anterior teeth 40 may even be removed completely, should the desired result be obtained on the anterior teeth 40 before the anchor molars 36 and 38 (and any other teeth affected by the primary wire arch 14) are fully repositioned.

The dual coil spring lingual arch 10 of the present invention may be utilized in any application wherein conventional orthodontic appliance for moving the anterior teeth 40 forward while separating molar teeth including the anchor molars 36 and 38 are used. The main area of improvement is in the ability to accomplish these purposes with a single appliance and in the ability to separately adjust the amount of pressure utilized in accomplishing each of these purposes.

Since the dual coil spring lingual arch 10 of the present invention may be readily constructed and are significantly similar to prior art conventional orthodontic appliances such that little or no special training will be required for the utilization thereof by practitioners, it is expected that they will be acceptable in the industry as substitutes for the conventional orthodontic appliances in many applications. For these and other reasons, it is expected that the utility and industrial applicability of the invention will be both significant in scope and long-lasting in duration.

I claim:

1. An orthodontic appliance for adjustment of molar teeth and further for adjustment of anterior teeth, comprising:
    a generally U-shaped primary spring wire arch having a curved center portion and two end portions, said end portions being adapted for exerting force against the molar teeth such that the molar teeth tend to be moved distally; and
    a secondary spring wire arch having a generally U-shaped anterior portion connected to the primary spring wire arch such that said anterior portion of the secondary spring wire arch may be placed against the anterior teeth with force against the anterior teeth being provided by means of compression of, at least a portion of the secondary spring wire arch between the primary spring wire arch and the anterior teeth.

2. The orthodontic appliance of claim wherein the secondary spring wire arch includes:
    a plurality of coil springs formed as a part of the secondary spring wire arch such that said coil springs are compressed between the anterior teeth and the primary spring wire arch to provide force against the anterior teeth relative to the primary spring wire arch.

3. The orthodontic appliance of claim 2, wherein:
    said coil springs are formed by wrapping a portion of the secondary spring wire arch around the primary spring wire arch.

4. The orthodontic appliance of claim 2, wherein:
    said end portions of the primary spring wire arch are attached by a practitioner to an opposed pair of the molar teeth.

5. The orthodontic appliance of claim 4, wherein:
    the secondary spring wire arch may be put into position against the anterior teeth after the primary spring wire arch is attached to said opposed pair of the molar teeth.

6. The orthodontic appliance of claim 5, wherein:
    the secondary spring wire arch is put into position against the anterior teeth by the action of manually lengthening said coil springs.

7. The orthodontic appliance of claim 4, wherein:
    pressure against the anterior teeth is a function of the unstressed shape of the primary spring wire arch, which unstressed shape may be adjusted by a practitioner after the orthodontic appliance is installed in the mouth of a patient.

8. The orthodontic appliance of claim 1, wherein:
    the secondary spring wire arch is connected at its ends along at least a portion of said end portions of the primary spring wire arch.

9. The orthodontic appliance of claim 1, wherein:
    pressure against the molar teeth is a function of the unstressed shape of the primary spring wire arch, which unstressed shape may be adjusted by a practitioner prior to the orthodontic appliance being installed in the mouth of a patient.

10. A device for moving molar teeth distally in a patient's mouth while also moving anterior teeth forward, comprising:
    a first wire spring having a curved first wire spring center portion integral with two first wire spring end portions, for positioning between opposed members of the molar teeth such that force is exerted by said first wire spring end portions against the molar teeth, which force tends to move the molar teeth apart distally; and
    a second wire spring having a curved second wire spring center portion integral with two second wire spring end portions, at least a portion of said second wire spring end portions including a plurality of turns around said first wire spring end portions such that each of said second wire spring end portions defines a coil;
    the second wire spring being joined to the first wire spring such that said curved second wire spring center portion is generally parallel to said first wire spring center portion and further such that compression of said coils tends to cause said second wire spring curved section to move away from said first wire spring curved section.

11. The device of claim 10, wherein;
    said first wire spring end portions are affixed to at least an opposed pair of the molar teeth.

12. The device of claim 10, wherein:
    said curved second wire spring center portion may be caused to exert force on the anterior teeth by the action of altering said coils such that the unstressed length of said coils is increased.

13. The device of claim 12, wherein:
    an amount of force exerted on the anterior teeth may be readjusted while the device is in place in the patient's mouth by the action of manually altering the unstressed length of said coils.

14. The device of claim 12, wherein:
    the unstressed length of said coils is altered by physically stretching or compressing said coils, as appropriate, past the limits of perfect elasticity of said coils such that said coils do not fully rebound to their original length.

15. A lingual arch for application to the mouth of a dental patient such that molar teeth and anterior teeth are spread apart in order to create room for the eruption of new teeth, comprising:
    a generally U-shaped primary wire arch having a curved center section integral with a right end leg section and a left end leg section, said end leg sections being adapted for connection to at least a pair of the molar teeth opposed distally across the mouth such that the primary wire arch is held in place in the mouth by the connection of said end leg sections to the molar teeth and further such that said end leg sections exert pressure outward against the molar teeth, which pressure tends to force the molar teeth apart distally; and a secondary wire arch having an anterior arch portion, a right coil spring and a left coil spring, said right coil spring being integral with said anterior arch portion at one end and further being affixed to said right end leg section of the primary wire arch at the other end, said left coil spring further being integral with said anterior arch portion at one end and further being affixed to said left end leg section of the primary wire arch at the other end, said right coil spring and said left coil spring being formed integrally with said anterior arch portion and further being formed such that said end leg sections of the primary wire arch are coaxial with said coil springs, the secondary wire arch being initially placed such that said anterior arch portion of the secondary wire arch is generally colinear with said curved center section of the primary wire arch.

16. The lingual arch of claim 15, wherein:

said anterior arch portion of the secondary wire arch can be extended forward in the mouth to exert pressure against the anterior teeth by the action of stretching said coil springs such that the unstressed length of said coil springs is elongated.

17. In an orthodontic appliance, the orthodontic appliance being of a type which is secured in the mouth of a patient for assisting in realigning teeth of the patient, an improvement comprising:

a wire spring arch having a generally U-shaped center section and two end sections, said center section being formed and positioned so as to be placed against the lingual side of anterior teeth for urging the anterior teeth forward; and a pair of spring means for connecting said ends of the spring wire arch to the orthodontic appliance such that said center section of the wire spring arch is urged toward the anterior teeth by means of force supplied by the spring means.

18. The improvement of claim 17, wherein:

the orthodontic appliance is connected to an opposed pair of molar teeth for moving the molar teeth distally within the mouth of the patient.

19. The improvement of claim 18, wherein:

each of the spring means is attached to one of a pair of sides of the orthodontic appliance.

20. The improvement of claim 18, wherein:

each of the spring means is a coil spring wound around one of said sides of the orthodontic appliance and connected thereto at one end of the spring means, with an opposite end of each of the spring means being integral with one of said end sections of the wire spring arch.

* * * * *